United States Patent [19]
Rasmussen

[11] Patent Number: 5,574,207
[45] Date of Patent: Nov. 12, 1996

[54] RYE GRASS HYBRID 1917 AND PARENTAL LINES 71548 AND 71550

[75] Inventor: Ross H. Rasmussen, Hooper, Nebr.

[73] Assignee: Nu-Dwarf Farms Inc., Hooper, Nebr.

[21] Appl. No.: 222,068

[22] Filed: Apr. 4, 1994

[51] Int. Cl.$^6$ .............................. A01H 1/02; A01H 5/00; A01H 5/10

[52] U.S. Cl. ................. 800/200; 800/250; 800/DIG. 52; 47/58; 47/DIG. 1

[58] Field of Search ............................... 47/58.01, 58.03, 47/DIG. 1, 58; 800/200, 250, DIG. 52

[56] References Cited

PUBLICATIONS

Allan. 1980, In Hybridization of Crop Plants. Fehr et al. (eds). p. 710.
Glossary of Crop Science Terms, 1992, Crop Science Society of America, p. 67.
Ahloowalia, 1981, Crop Science, 21:415–418.
Ahloowalia, 1977, Theor. Appl. Genet. 49:299–235.
Utz et al. 1978, Z. Pflanzenzuchtg, 80:223–229.
Jones et al. 1981, J. Agric. Sci., Comb. 96:521–537.

*Primary Examiner*—Erich E. Veitenheimer
*Attorney, Agent, or Firm*—Rothwell, Figg, Ernst & Kurz, P.C.

[57] ABSTRACT

Rye grass lines, designated 71548 and 71550 are disclosed. The invention relates to the seeds of inbred rye grass lines 71548 and 71550, to the plants of inbred rye grass lines 71548 and 71550 and to methods for producing a rye grass plant by crossing the inbred lines 71548 or 71550 with itself or another rye. grass line. The invention further relates to hybrid rye grass seeds and plants produced by crossing the inbred lines 71548 or 71550 with another annual wheat or annual rye grass line.

26 Claims, No Drawings

RYE GRASS HYBRID 1917 AND PARENTAL LINES 71548 AND 71550

BACKGROUND OF THE INVENTION

The present invention relates to a new and distinctive hybrid perennial rye grass, designated 1917 and the parental lines 71548 and 71550. There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety or hybrid an improved combination of desirable traits from the parental germplasm. These important traits may include higher yield, resistance to diseases and insects, tolerance to drought and heat, and better agronomic quality.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, and mass selection.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

These processes, which lead to the final step of marketing and distribution, usually take from eight to 20 years from the time the first cross is made. Therefore, development of new cultivars is a time-consuming process that requires precise forward planning, efficient use of resources, and a minimum of changes in direction.

The breeder initially selects and crosses two or more parental lines, followed by repeated selfing and selection, producing many new genetic combinations. The breeder can theoretically generate billions of different genetic combinations via crossing, selfing and mutations. The breeder has no direct control at the cellular level. Therefore, two breeders will never develop the same line, or even very similar lines, having the same rye grass traits.

Each year, the plant breeder selects the germplasm to advance to the next generation. This germplasm is grown under unique and different geographical, climatic and soil conditions, and further selections are then made, during and at the end of the growing season. The inbred lines which are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce the same line twice by using the exact same original parents and the same selection techniques.

Today's standard procedure for grass breeding is to select a population of the best plants, plant and then re-select again. This breeding and testing process gains uniformity through family selfing and crossing and may provide a new grass which can be named and sold to the general public. Examples include Nebraska 28 Switchgrass and Pawnee Big Bluestem, all developed by Dr. Lawrence Newell, U.S.D.A., located at the University of Nebraska at Lincoln.

Perennial rye grass is a valuable field crop. Currently, the rancher-farmer who desires a growing grass from early spring until late fall must have separate pastures, one of which is called a cool season pasture which will provide grazing early in the spring and in the late fall. A warm season pasture is used for the mid-season, during the warmer portion of the growing season. This warm season grass does not grow in the spring until frost has stopped and then grows only until the frost returns again in the fall. It is costly for the rancher-farmer to provide additional acres so that he can have both the cool season and the warm season pastures available for grazing. A cool season pasture normally goes dormant with air temperatures above 90° F. A cool season grass also produces seed at the end of the cool spring season which triggers the plant dormancy period with reduced plant growth. Most grass plants provide vigorous growth up to and until seed production is completed. It would be very desirable to have a perennial rye grass which would produce vegetation growth during the whole growing season and eliminate the need for the separate pastures required for both warm-season and cool-season grasses. It also is desirable to have a rye grass which is awnless or with a very short awn to allow easier seed handling and planting.

SUMMARY OF THE INVENTION

According to the invention, there is provided a novel rye grass hybrid, designated 1917 and its parental lines 71548 and 71550. This invention thus relates to the seeds of rye grass lines 71548 and 71550, to the plants of rye grass lines 71548 and 71550 and to methods for producing a rye grass plant produced by crossing either rye grass line 71548 or 71550 with itself or another annual wheat or annual rye grass plant. This invention further relates to hybrid rye grass seeds and plants produced by crossing the rye grass line 71548 with line 71550.

DEFINITIONS

In the description and tables which follow, a number of terms are used. In order to provide a clear and consistent understanding of the specification and claims, including the scope to be given such terms, the following definitions are provided:

Awn Length. The awn length is measured from the top of the outer glume where the awn begins to the end tip of the awn.

Protein percentage. The protein percentage is calculated in percent of total dry weight. For example the protein percentage of 0.55 for alanine (as shown in Table 1) is calculated by dividing the total alanine dry weight by the total weight of the dry matter of the sample used.

DETAILED DESCRIPTION OF THE INVENTION

Rye grass lines designated 71548 and 71550 are inbred lines with superior characteristics, and provide excellent parental lines for producing the first generation ($F_1$) hybrid rye grass designated 1917.

The parents of 71548 and 71550 were probably derived from natural crossings of Canada Wild Rye grass and Virginia Wild Rye grass. Rye grass 71548 was developed from a 1984 selection in Dodge County, Nebr. This 1984 selection had a shorter awn length. After several selections, 71548 was developed, having a short awn, full season of plant growth, excellent vegetative plant growth, continuous seed production from mid-season to late fall, good seed set and increased grain yield potential.

Rye grass 71550 was developed from a 1985 selection in Washington County, Nebraska. After several selections, 71550 was developed having dense vigorous growth, an awnless characteristic, and increased crude protein level as shown in Table 1.

For rye grass plants to cross pollinate in nature, the plants which are to cross must freely shed pollen during the same period of time. These rye grass plants are more receptive of foreign (unrelated genetic background) pollen when available and will tend to reject their own pollen. It is known that unrelated rye grass plants will more readily cross and more closely related lines will not as readily cross pollinate. The selection process for the development of the Dodge and Washington County inbred lines followed these guidelines.

When a mix of the Dodge and Washington County inbred lines are planted in an isolated crossing field, a free open cross pollination results in a cross on each plant of the endosperm and embryo for each seed, which occurs at the same period of time.

During this first growing season, the endosperm will increase in size because of hybrid vigor resulting from an unrelated cross, as shown in Table 2. During this first growing season and within the same seed, the embryo develops with a viable germ and with a genetic base of 71548×71550 and/or 71550×71548. In the next season of growth, the $F_1$ generation of the embryo will be expressed. It will provide a high level of hybrid vigor, as shown in Table 2.

These rye grass inbreds 71548 and 71550 and the hybrid 1917 have shown uniformity and stability for all traits.

The hybrid 1917 is produced by crossing 71548 with 71550. Seed of these two lines is mixed together and planted in an open pollinated field, resulting in nearly 100 percent $F_1$ seed production. Hybrid 1917 is characterized by superior protein quantity and seed quality. The hybrid 1917 also has the following characteristics: 1) Seed which can easily be cleaned and planted, because of its short awn, 2) excellent full season vegetative growth, 3) little or no seed dormancy, 4) ability to be seeded in either the fall or the spring, 4) when grazed, seed heads are produced from mid summer and into the fall, 5) adapted to many diverse soil types, and 6) increased plant vigor with an enlarged seed head and vigorous vegetative and rhizome growth.

Another object of the present invention is to utilize the hybrid vigor of the $F_1$ endosperm in the first generation of seed production and which is expressed prior to the expression of the $F_1$ embryo. As shown in Table 2, this $F_1$ endosperm vigor results in an increased seed size and weight per 100 seeds. Table 1 shows the next generation after the $F_1$ endosperm generation which allows the expression of the $F_1$ embryo. The $F_1$ embryo and $F_1$ endosperm are developed at the same period of time and from the same germ plasm. The difference being that the expression of the $F_1$ embryo is not expressed until after it has germinated in the $F_1$ embryo generation and has produced a growing plant for the next generation. The genetic base of the $F_1$ endosperm end with the current generation of the cross of the two inbred lines. Since rye grass is a perennial, this $F_1$ plant vigor can be maintained over several to many years. Additional generations after the $F_1$, have reduced levels of hybrid vigor.

When seed from a perennial rye grass production field is sold, this seed will continue to provide the high hybrid vigor and high protein level year after year. This hybrid production system will only work when two unrelated parental inbred lines are used which are compatible and complimentary for numerous important traits. There is no known use of hybrid vigor of the endosperm and its use in seed production for providing seed for commercial sales year after year. Also there is no known use of the fact that the $F_1$ endosperm and $F_1$ embryo are expressed at different periods of time and can be utilized advantageously in both perennial and annual plants.

The 1917 hybrid provides superior seed size and forage production. The 1917 hybrid is 6 to 8 inches taller than either 71548 or 71550.

The most related prior art to the instant invention is the Canada wild rye grass which was probably in the parentage of both the 71548 and 71550 lines. Canada Wild Rye grass has lower overall protein quantity with few to no rhizomes present.

| VARIETY DESCRIPTION INFORMATION for 71548 | |
| --- | --- |
| Spikelets | Appearing in pairs but occurrence along the rachis is of the density throughout. Pairs also appear symmetrically. |
| Glumes | Hispid at the apex gradually becoming less, glaborous at the base. |
| Lemmas & Paleas | Hispid from base to apex including awn. Ribbing or variation not always clearly visible. |
| Ligule | No hairs. Membranous and is toothlike with wide gaps in membrane that are rounded at the bottom. Leaf blade is not as broad and clasping at the base near ligule. |
| Awn | Short awn, less than 12 mm |
| Weight of 100 Seeds | 0.412 grams |

| VARIETY DESCRIPTION INFORMATION for 71550 | |
| --- | --- |
| Spikelets | Appearing in pairs, less dense at the base, more tightly clustered at the top. Pairs appear symmetrically with inner glumes a bit longer than outer glumes. Hispid at the apex gradually becoming less, glaborous at base. |
| Glumes | Subulate - aristate. |
| Lemmas & Paleas | Subulate - aristate. |
| Ligule | No hairs. Tooth like gaps that resemble tears, clearly ribbed where grasping the stem opposite the blade. |
| Awn | No awn. |
| Weight of 100 Seeds | 0.385 grams |

This invention is also directed to methods for producing a rye grass plant by crossing a first parent rye grass plant with a second parent rye grass plant, wherein the first or second rye grass plant is the inbred rye grass plant from either line 71548 or 71550. Therefore, any methods using the rye grass lines 71548 or 71550 are part of this invention: selfing, backcrosses, hybrid breeding, and crosses to populations. Any plants produced using either inbred rye grass lines 71548 or 71550 as a parent are within the scope of this invention. Advantageously, the inbred rye grass lines are used to produce the hybrid cross 1917.

As used herein, the term "plant" includes plant cells, plant protoplasts, plant cell of tissue culture from which rye grass plants can be regenerated, plant calli, plant clumps, and plant cells that are intact in plants or parts of plants, such as pollen, flowers, leaves, husks, stalks, and the like.

TABLES

In the tables that follows, the protein and characteristics are presented for the inbred rye grass lines 71548 and 71550, hybrid 1917 and prior art Canada Wild Rye.

TABLE 1

SEED WEIGHTS AND PROTEIN ANALYSIS OF THE SEED
100 seed weight in grams is calculated as the mean of 6 replications. All other numbers are in percent by weight and also represents the mean of 6 replications of data.

| | GENOTYPES | | | |
|---|---|---|---|---|
| | 71548 Dodge Co. | 71550 Washington Co. | 1917 Hybrid Dodge × Washington | Canada Wild Rye |
| 100 Seed Wt. (gr) | .412 | .385 | .480 | .444 |
| Total Weight of Dry Matter | 93.51 | 93.76 | 93.52 | 94.53 |
| Crude Protein | 16.81 | 20.24 | 20.20 | 16.10 |
| Alanine | .55 | .61 | .62 | .52 |
| Arginine | .70 | .75 | .70 | .57 |
| Aspartic Acid | .66 | .71 | .73 | .68 |
| Cystine | .31 | .33 | .32 | .23 |
| Glutamic Acid | 4.87 | 5.78 | 5.83 | 3.67 |
| Glycine | .66 | .77 | .77 | .62 |
| Histidine | .34 | .38 | .39 | .28 |
| Isoleucine | .54 | .64 | .63 | .47 |
| Leucine | 1.13 | 1.30 | 1.32 | .92 |
| Lysine | .40 | .43 | .44 | .44 |
| Methionine | .30 | .32 | .30 | .25 |
| Methionine & Cystine | .61 | .65 | .63 | .47 |
| Phenylalanine | .78 | .95 | .94 | .67 |
| Proline | 1.65 | 2.00 | 1.96 | 1.30 |
| Serine | .80 | .90 | .94 | .67 |
| Threonine | .58 | .67 | .67 | .53 |
| Tryptophan | .00 | .00 | .00 | .00 |
| Tyrosine | .57 | .66 | .69 | .41 |
| Valine | .77 | .86 | .89 | .69 |

TABLE 2

ENDOSPERM AND SEED WEIGHTS
100 seed weight in grams was calculated as the mean of 6 replications

| Seed Harvested From Genotype | 100 Seed Weight |
|---|---|
| 71548 Dodge Co. | .412 |
| 71550 Washington Co. | .385 |
| $F_1$ Hybrid 1917 plant Dodge × Washington | .480 |
| Dodge Co. female plant; After being crossed with Washington Co. as the male pollinator | .410 |
| Washington Co. female plant; After being crossed with Dodge Co. as the male pollinator | .405 |

DEPOSIT INFORMATION

Seeds of 71548 have been placed on deposit with the American Type Culture Collection (ATCC), Rockville, Md. 20852, under Deposit Accession Number 75707 on Mar. 16, 1994.

Seeds of 71550 have been placed on deposit with the American Type Culture Collection (ATCC), Rockville, Md. 20852, under Deposit Accession Number 75706 on Mar. 16, 1994.

Although the foregoing invention has been described in some detail by way of illustration and example for purposes of clarity and understanding, it will be obvious that certain changes and modifications may be practiced within the scope of the invention, as limited only by the scope of the appended claims.

What is claimed is:

1. Inbred rye grass seed designated 71548 having ATCC accession No. 75707.

2. A rye grass plant produced by growing the seed of claim 1.

3. Pollen of the plant of claim 2.

4. An ovule of the plant of claim 2.

5. An inbred rye grass plant having all the physiological and morphological characteristics of the rye grass plant of claim 2.

6. Inbred rye grass seed designated 71550 having ATCC Accession No. 75706.

7. A rye grass plant produced by growing the seed of claim 6.

8. Pollen of the plant of claim 7.

9. An ovule of the plant of claim 7.

10. An inbred rye grass plant having all the physiological and morphological characteristics of the rye grass plant of claim 7.

11. A method for producing first generation ($F_1$) hybrid rye grass seed comprising crossing a first rye grass plant with a second rye grass plant and harvesting the resultant first generation ($F_1$) hybrid rye grass seed, wherein said first or second rye grass plant is the rye grass plant of claim 2.

12. The method of claim 11 wherein said rye grass plant of claim 2 is the female plant.

13. The method of claim 11 wherein said rye grass plant of claim 2 is the male parent.

14. A first generation ($F_1$) hybrid rye grass plant produced by growing hybrid rye grass seed, wherein said seed is produced by crossing a first parent rye grass plant with a second rye grass plant, wherein said first or second inbred rye grass plant is the rye grass plant of claim 2, and harvesting the resultant first generation ($F_1$) hybrid rye grass seed.

15. A first generation perennial ($F_1$) hybrid plant produced by growing hybrid seed, wherein said seed is produced by crossing a first parent rye grass plant with a second parent wheat plant, wherein said first parent rye grass plant is the rye grass plant of claim 2.

16. A first generation ($F_1$) hybrid plant produced by growing hybrid. seed, wherein said seed is produced by crossing a first parent rye grass plant with a second parent annual rye plant, wherein said first parent rye grass plant is the rye grass plant of claim 2.

17. A method for producing first generation ($F_1$) hybrid rye grass seed comprising crossing a first rye grass plant with a second rye grass plant and harvesting the resultant first generation ($F_1$) hybrid rye grass seed, wherein said first or second rye grass plant is the rye grass plant of claim 7.

18. The method of claim 17 wherein said rye grass plant of claim 7 is the female plant.

19. The method of claim 17 wherein said rye grass plant of claim 7 is the male parent.

20. A first generation ($F_1$) hybrid rye grass plant produced by growing hybrid rye grass seed, wherein said seed is produced by crossing a first parent rye grass plant with a second rye grass plant, wherein said first or second inbred rye grass plant is the rye grass plant of claim 7, and harvesting the resultant first generation ($F_1$) hybrid rye grass seed.

21. A first generation perennial ($F_1$) hybrid plant produced by growing hybrid seed, wherein said seed is produced by crossing a first parent rye grass plant with a second parent wheat plant, wherein said first parent rye grass plant is the rye grass plant of claim 7.

22. A first generation ($F_1$) hybrid plant produced by growing hybrid seed, wherein said seed is produced by crossing a first parent rye grass plant with a second parent annual rye plant, wherein said first parent rye grass plant is the rye grass plant of claim 7.

23. A method of improving endosperm hybrid vigor in an $F_1$ rye grass seed, wherein said seed is produced by crossing a first rye grass plant with a second rye grass plant and harvesting the resultant first generation ($F_1$) hybrid rye grass endosperm and embryo, wherein said first or second rye grass plant is the rye grass plant of claim 2.

24. A method of improving endosperm hybrid vigor in an $F_1$ rye grass seed, wherein said seed is produced by crossing a first rye grass plant with a second rye grass plant and harvesting the resultant first generation ($F_1$) hybrid rye grass endosperm and embryo, wherein said first or second rye grass plant is the rye grass plant of claim 7.

25. A first generation hybrid plant produced by growing seed, wherein said seed is produced by crossing a first parent hybrid plant with a second parent hybrid plant, wherein said first parent hybrid plant is the plant of claim 15, and wherein said second parent hybrid plant is the plant of claim 21.

26. A first generation hybrid plant produced by growing seed, wherein said seed is produced by crossing a first parent hybrid plant with a second parent hybrid plant, wherein said first parent hybrid plant is the plant of claim 16, and wherein said second parent hybrid plant is the plant of claim 22.

* * * * *